US004001705B2

United States Statutory Invention Registration [19]

[11] Reg. Number: H1705

[45] Published: Jan. 6, 1998

Dumas et al.

[54] PROCESS FOR PREPARING 2-CARBOALKOXY-1-INDANONES

[75] Inventors: Donald Joseph Dumas, Wilmington, Del.; William Christopher Hollinsed, Rutledge, Pa.

[73] Assignee: E. I. du Pont de Nemours and Company, Wilmington, Del.

[21] Appl. No.: 847,410

[22] Filed: Apr. 28, 1997

[51] Int. Cl.[6] ..... C07C 69/76

[52] U.S. Cl. ..... 560/51

*Primary Examiner*—Charles T. Jordan
*Assistant Examiner*—Meena Chelliah
*Attorney, Agent, or Firm*—Elliott A. Katz

[57] ABSTRACT

A process for the preparation of 2-carboalkoxy-1-indanones of Formula I from 1-indanones of Formula II using a dialkyl carbonate and an alkali metal alkoxide is provided. This process is superior to the prior art in that it avoids pyrophoric reagents such as sodium hydride, and proceeds in high chemical yield and product quality. The invention provides a novel process to an important intermediate in the preparation of arthropodicidal carboxanilides of commercial interest.

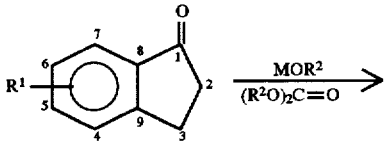

II

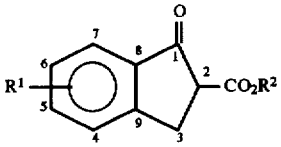

I wherein:

$R^1$, $R^2$ and M are defined in the specification.

6 Claims, No Drawings

PROCESS FOR PREPARING 2-CARBOALKOXY-1-INDANONES

This application claims the priority benefit of U.S. Provisional Application 60/018,094, filed May 22, 1996.

BACKGROUND OF THE INVENTION

1. Field of Invention

This invention relates to processes for preparing 2-carboalkoxy-1-indanones, particularly 2-carbomethoxy-5-chloro-1-indanone.

2. Background

It is known that certain 2-carbomethoxy-1-indanones can be prepared by treatment of the corresponding 1-indanones with dimethyl carbonate in the presence of sodium hydride.

2-Carboalkoxy-1-indanones are useful intermediates for a variety of organic compounds including a new class of arthropodicidal carboxanilides described in EP A565544.

The need exists for a more efficient process to prepare these intermediates from the corresponding 1-indanones.

SUMMARY OF THE INVENTION

According to the present invention there is provided processes for the preparation of 2-carboalkoxy-1-indanones of Formula I:

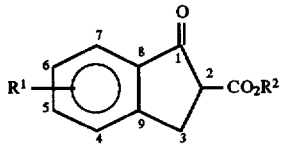

I comprising reacting a 1-indanone of Formula II

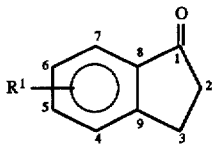

II with at least one molar equivalent of a dialkyl carbonate of the formula $(R^2O)_2C{=}O$ in an aprotic solvent in the presence of a base $MOR^2$ and removing alcohol $R^2OH$ by distillation as it is formed from the reaction of the indanone of Formula I with the dialkyl carbonate wherein:

$R^1$ is selected from the group H, $R^3$, $C_2$–$C_6$ alkoxyalkyl, $C_2$–$C_6$ alkylthioalkyl, $C_3$–$C_6$ cycloalkyl, $C_3$–$C_6$ fluorocycloalkyl, halogen, $OR^3$, $SR^3$, $S(O)R^3$, $S(O)_2CF_3$, $S(O)_2CF_2R^3$, $OS(O)_2R^3$, $CO_2R^2$, $NR^3R^4$, $NO_2$, phenyl optionally substituted with 1 to 3 substituents independently selected from $R^5$ and benzyl optionally substituted with 1 to 3 substituents independently selected from $R^5$;

$R^2$ is $C_1$–$C_6$ alkyl;

$R^3$ is selected from the group $C_1$–$C_6$ alkyl, and $C_1$–$C_6$ fluoroalkyl;

$R^4$ is $C_1$–$C_4$ alkyl;

$R^5$ is selected from the group halogen, $NO_2$, $C_1$–$C_2$ alkyl, $C_1$–$C_2$ fluoroalkyl, $C_1$–$C_2$ alkoxy, $C_1$–$C_2$ fluoroalkoxy, $C_1$–$C_2$ alkylthio, $C_1$–$C_2$ fluoroalkylthio, $SO_2CF_3$, $SO_2CF_2R^3$, and M is an alkali metal.

Preferred for reasons of greater commercial utility and/or ease of synthesis is the process wherein: $R^1$ is halogen, and $R^2$ is $C_1$–$C_3$ alkyl.

More preferred is the process wherein: $R^1$ is Cl, $R^2$ is $C_1$–$C_3$ alkyl, and M is sodium or potassium.

Most preferred is the process wherein: $R^1$ is Cl at the 5-position, $R^2$ is $CH_3$ and M is sodium.

The processes of the present invention can be used to avoid the use of pyrophoric agents such as sodium hydride, and proceed in high chemical yield with good product quality.

In the above recitations, the term "alkyl", used either alone or in compound words such as "alkylthio" or "fluoroalkyl" includes straight-chain or branched alkyl, such as, methyl, ethyl, n-propyl, i-propyl, or the different butyl, pentyl or hexyl isomers. "Alkoxy" includes, for example, methoxy, and ethoxy. "Alkylthio" includes branched or straight-chain alkylthio moieties such as methylthio, and ethylthio.

The term "halogen" includes fluorine, chlorine, bromine or iodine. When used in compound words such as "fluoroalkyl", said alkyl may be partially or fully substituted with fluorine atoms which may be the same or different. Examples of "fluoroalkyl" include $F_3C$, $FCH_2$, $CF_3CH_2$ and $CF_3CF_2$. The term "fluoroalkoxy" is defined analogously to the term "fluoroalkyl". Examples of "fluoroalkoxy" include $CF_3O$, and $CF_3CH_2O$. Examples of "fluoroalkylthio" include $CF_3S$, and $CF_3CH_2S$.

The total number of carbon atoms in a substituent group is indicated by the "$C_i$–$C_j$" prefix where i and j are numbers from 1 to 6. For example, $C_1$–$C_2$ alkoxy designates $CH_3O$ and $CH_3CH_2O$; $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples include $CH_3CH_2CH_2OCH_2$ and $CH_3CH_2OCH_2CH_2$.

DETAILS OF THE INVENTION

The compounds of Formula I can be prepared by the process of this invention which comprises the process variations as described below.

The solvent used in the process of this invention can be any non-reactive, aprotic solvent which when combined with the reactants used in the process of the present invention forms a reaction mixture from which the alcohol produced as a byproduct of this invention, such as methanol, can be separated by distillation. Depending on the specific reaction conditions, the alcohol can be removed as: (a) the alcohol; (b) an azeotrope or mixture of the alcohol and dialkyl carbonate; (c) an azeotrope or mixture of the alcohol and solvent; or, (d) an azeotrope or mixture of the alcohol, dialkyl carbonate and solvent. Preferred for ease of operation, cost, toxicity and environmental reasons are solvents selected from aromatic hydrocarbons, chlorobenzene, dichlorobenzenes, aliphatic hydrocarbons and dialkyl carbonates. More preferred are toluene, xylenes, chlorobenzene, dichlorobenzenes, heptane and dimethyl carbonate.

The alcohol or alcohol containing component can be distilled from the reaction mixtures using equipment and techniques known to those skilled the art. Equipment and procedures which allow for efficient removal of alcohol while minimizing co-distillation of dialkyl carbonate and/or solvent are preferred. This can be achieved using conventional fractional distillation equipment.

The reaction is most conveniently run at the boiling point of the reaction mixture at ambient pressure. Reaction temperatures need to be at least equal to the boiling point of the byproduct alcohol (e.g., methanol) or of the alcohol containing azeotrope or mixture being removed. Preferably the reaction is carried out at temperatures between 60° and 150° C. More preferably between 80° and 120° C.

For reasons of ease of operation and safety, the reaction is preferably run substantially in the absence of alkali metal hydrides like sodium hydride, to avoid their pyrophoric nature and mineral oil coating. The mineral oil coating can be difficult to remove and process on a commercial scale. The alkali metal alkoxide used in the process of the present invention avoids the process disadvantages of the alkali metal hydrides.

Any alkali metal alkoxide can be used, preferably sodium or potassium methoxide, but sodium methoxide is preferred for reasons of cost and availability.

In principle, only about one molar equivalent of alkali metal alkoxide is needed although any amount in excess of one molar equivalent an be used. High conversions of the 1-indanone (5-chloro-1-indanone) can be obtained using between 1.0 and 1.5 equivalents of metal alkoxide. Preferably between 1.0 and 1.2 equivalents are employed. In some cases the 5-chloro-1-indanone can be contaminated with other 1-indanones. In these instances, the molar amount of alkali metal alkoxide employed should be relative to the total amount of 1-indanones present.

In principle, only one molar equivalent of dialkyl carbonate (preferably dimethyl carbonate) is needed. However, sufficient dimethyl carbonate should be employed so as to allow for losses of dimethyl carbonate via co-distillation with the methanol (methanol forms an azeotrope with dimethyl carbonate which boils at 62.7° C. and contains about 70% methanol) and solvent. Preferably between 1.5 and 5.0 equivalents can be used, more preferably between 2.0 and 4.0 equivalents.

The reagents should be combined at a rate such that the byproduct methanol produced is promptly and efficiently removed to avoid the formation of side-reaction products which adversely affect the purity and yield of the desired product. The 5-chloro-1-indanone can be dissolved or slurried with the solvent and optionally mixed with all or part of the dimethyl carbonate and then added over time to a mixture of sodium methoxide and solvent (optionally containing all or part of the dimethyl carbonate) which has been preheated to the appropriate reaction temperature. Alternatively the sodium methoxide mixture can be added over time to the 5-chloro-1-indanone/dimethyl carbonate mixture which has been preheated to the appropriate reaction temperature. For best results, it is preferred that the 5-chloro-1-indanone containing mixture be added to the sodium methoxide containing mixture.

To avoid mixed esters, which might result from ester interchange, the dialkyl carbonate, $(R_2O)_2C=O$, and the metal alkoxide, $MOR^2$, should be derived from the same alcohol.

The process is most conveniently operated at atmospheric pressure, but depending on the boiling point of the alcohol, dialkyl carbonate and solvent, the process may also be conducted under reduced or elevated pressure.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; s=singlet, d=doublet, t=triplet, dd=doublet of doublets.

EXAMPLE 1

Preparation of 5-chloro-2-methoxycarbonyl-1-indanone

A 1 L, 4-neck round bottom flask was equipped with an overhead stirrer with an oval paddle, thermometer, liquid feed line with an FMI pump, five tray Oldershaw column with a variable takeoff head and nitrogen inlet, and a heating mantel. The system was set up so that temperature could be monitored in the pot, at each tray of the Oldershaw column and at the distillation head. Circulation of 5° C. water through the condenser was initiated. The flask was charged with 15.7 g (0.275 mol) of Aldrich 95% sodium methoxide, 350 mL of toluene and 22 mL (0.26 tool) of Aldrich 99% dimethyl carbonate (DMC) and heated to reflux. The pot and head temperatures were 108.5° C. and 88° C., respectively. Column temperatures, from bottom to top, were 103° C., 99° C., 95° C., 91° C. and 89° C. A solution of 41.7 g (0.25 mol) of 5-chloro-1-indanone, 250 mL of toluene and 41.8 mL (0.49 mol) of DMC was then pumped in at a rate of about 1.7 mL/min over 3 h and 6 min. Once the temperature at the fourth tray (counting from the bottom) of the column dropped below 70° C., takeoff off methanol/DMC/toluene distillate was initiated at such a rate as to maintain the temperature at the fourth tray at 65°–70° C. After addition was complete, the feed solution was rinsed in with two 5 mL portions of toluene. Distillate was collected until the head temperature reached 92° C. This required an additional 34 min after the completion of the addition. The pot temperature was 109° C. and the column temperatures, from bottom to top, were 104° C., 101° C., 97° C., 94° C. and 93° C. A total of 44 mL (38.0 g) of distillate was collected. The receiver was replaced and the take off rate increased. An additional 109 mL (97.8 g) of distillate was collected over 35 min. The final pot and head temperatures were 111° C. and 108° C., respectively. Column temperatures were 109° C., 109° C., 109° C., 108° C. and 108° C. The reaction mixture was cooled with water and then ice to 20° C. and solid product collected and washed successively with two 50 mL portions of toluene to leave 67 g of gray green solid after drying in a vacuum oven at about 50° C. The solid was suspended in 250 mL of water, the slurry cooled to 10° C. and 23 mL of concentrated hydrochloric acid added dropwise over 12 rain while maintaining the temperature below 10° C. The reaction mixture was then allowed to warm to room temperature and 500 mL of toluene added. Once all of the solids had dissolved, the phases were separated and the organic phase washed successively with 100 mL of water, 0.5 M sodium bicarbonate solution (two times with 100 mL portions) and again with water (three times with 100 mL portions) and dried over magnesium sulfate. The solvent was removed under reduced pressure and the tan solid product dried to a constant weight in a vacuum oven at about 50° C. to leave 54.8 g of tan solid which assayed (HPLC, 4.6×150 mm 5-micron, Zorbax® SB-C8 column and eluting at 1.5 mL per rain with 30% acetonitrile and 70% of a 0.1% solution of triethylamine in water pH adjusted to 6.5 with 85% phosphoric acid, 40° C., UV detector set at 254 nm) as 99% 5-chloro-2-methoxycarbonyl-1-indanone (96% yield). m.p. 82°–84° C..

EXAMPLE 2

5-Chloro-2-Carbomethoxy-1-Indanone Using Dimethyl Carbonate as the Solvent

To a 1 liter resin kettle equipped for simple distillation was added 300 mL of DMC. This was mechanically stirred and heated to boiling. When the pot and head temperatures reached ca. 90° C. and distillate started to come over, a solution Of 25% sodium methoxide in methanol (41 mL, 180 mmol) was added to the flask at a rate of ca. 1 mL per min. After a 5 min. delay, a solution of 5-chloro-1-indanone (20 g (120 mol); 120 mL total volume in DMC) was added at a rate of ca. 3 mL/min. The head temperature dropped to 65° to 75° C. and the methanol-dimethyl carbonate azeotrope distilled out of the reaction mixture as methanol was formed in the reactions and from the methanolic base solution. At the completion of both additions, some additional DMC was added to thin out the viscous reaction slurry and the reaction mixture was cooled to 10° C. The mixture was acidified with 15 mL of concentrated HCl dissolved in 100 mL of water and allowed to warm to room temperature. The two phase mixture was separated and the organic phase evaporated to dryness. The resulting solid dissolved in 100 mL of methanol and added to a rapidly stirring flask containing 250 mL of water. The resulting tan solid was filtered and dried yielding 24.32 g. $^1$H NMR: δ3.34, (dd,1H), (J=8, 18 Hz), δ3.55, (dd,1H) (J=4, 18 Hz), δ3.75, (dd,H) (J=4,8 Hz), δ3.79, (s,3H), δ7.37, (d,1H), (J=8 Hz), δ7.49, (s,1H), δ7.69, (d,1H), (J=8 Hz).

EXAMPLE 3

5-Chloro-2-Carbomethoxy-1-Indanone Using Xylene as the Solvent

Solid sodium methoxide (1.0 g, 18.5 mmol) was added to 30 mL of xylenes. The mixture was stirred and heated to 96° C. To this hot mixture was added a solution of 1.8 g ( 10.8 mmol) of 5-chloro-1-indanone in 9.1 mL of DMC. The chloro-1-indanone solution was added at a rate sufficient to permit removal of methanol formed in the reaction as its azeotrope with DMC (distillation head temperature was 64° C.). Upon completion of the addition, the mixture was cooled and a solution of 1.25 mL of concentrated HCl in 4 mL water was added. The phases were separated and the xylene phase was washed with water and the solvent removed by evaporation yielding 3.14 g of brown solid. This was recrystallized from methanol yielding 2.15 g of tan crystalline solid which was identical to the product of Example 2 by $^1$H NMR.

EXAMPLE 4

2-Carbomethoxy-1-Indanone

Solid sodium methoxide (1.0 g, 18.5 mmol) was added to 30 mL of toluene. The mixture was stirred and heated to 96° C. To this hot mixture was added a solution of 1.8 g ( 13.6 mmol) of 1-indanone in 9.1 mL of DMC. The indanone solution was added at a rate sufficient to permit removal of methanol formed in the reaction as its azeotrope with either DMC or toluene (distillation head temperature was 64° C.). Upon completion of the addition, the mixture was cooled and a solution of 1.25 mL of concentrated HCl in 4 mL water was added. The phases were separated and the toluene phase was washed with water and the solvent removed by evaporation yielding 2.22 g. $^1$H NMR: δ3.38, (dd,1H), (J=8, 17 Hz), δ3.58, (dd,1H) (J=4,17 Hz), δ3.75, (dd,1H) (J=4,8 Hz), δ3.80, (s,3H), δ7.40, (t,1H), δ7.51,(d,1H), δ7.64,(t,1H), δ7.79,(d,1H).

What is claimed is:

1. The process for the preparation of a 2-carboalkoxy-1-indanone of Formula I:

I

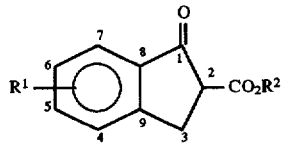

comprising reacting a 1-indanone of Formula II

II

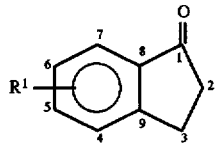

with at least one molar equivalent of a dialkyl carbonate of the formula $(R^2O)_2$ C=O in an aprotic solvent in the presence of a base $MOR^2$ and removing alcohol $R^2OH$ by distillation as it is formed from the reaction of the indanone of Formula I with the dialkyl carbonate wherein:

$R^1$ is selected from the group H, $R^3$, $C_2$–$C_6$ alkoxyalkyl, $C_2$–$C_6$ alkylthioalkyl, $C_3$–$C_6$ cycloalkyl, $C^3$–$C_6$ fluorocycloalkyl, halogen, $OR^3$, $SR^3$, $S(O)R^3$, $S(O)_2CF_3$, $S(O)_2CF_2R^3$, $OS(O)_2R^3$; $CO_2R^2$, $NR^3R^4$, $NO_2$, phenyl optionally substituted with 1 to 3 substituents independently selected from $R^5$ and benzyl optionally substituted with 1 to 3 substituents independently selected from $R^5$;

$R^2$ is $C_1$–$C_6$ alkyl;

$R^3$ is selected from the group $C_1$–$C_6$ alkyl, and $C_1$–$C_6$ fluoroalkyl;

$R^4$ is $C_1$–$C_4$ alkyl;

R5 is selected from the group halogen, $NO_2$, $C_1$–$C_2$ alkyl, $C_1$–$C_2$ fluoroalkyl, $C_1$–$C_2$ alkoxy $C_1$–$C_2$ fluoroalkoxy, $C_1$–$C_2$ alkylthio, $C_1$–$C_2$ fluoroalkylthio, $SO_2CF_3$, $SO_2CF_2R^3$, and M is an alkali metal.

2. A process of claim 1 wherein $R^1$ is Cl at the 5-position, $R^2$ is $CH_3$, and M is Na.

3. A process of claim 1 wherein the aprotic solvent is selected from aromatic hydrocarbons, chlorobenzene, dichlorobenzenes, aliphatic hydrocarbons and dialkyl carbonates.

4. A process of claim 3 wherein the aprotic solvent is selected from toluene, xylenes, chlorobenzene, heptane and dimethyl carbonate.

5. A process of claim 4 wherein $R^1$ is Cl at the 5-position, $R^2$ is $CH_3$ and M is Na.

6. A process of claim 5 wherein the alcohol $R^2OH$ is removed by continuous fractional distillation.

* * * * *